United States Patent [19]

Stephens et al.

[11] Patent Number: 4,739,770
[45] Date of Patent: Apr. 26, 1988

[54] FLUSH DEVICE

[75] Inventors: Thomas P. Stephens, Boxford; Robert G. Graves, Marblehead; Albert K. Bond, Burlington; David A. Bristol, Lynnfield, all of Mass.

[73] Assignee: Hewlett-Packard Company, Palo Alto, Calif.

[21] Appl. No.: 865,510

[22] Filed: May 21, 1986

[51] Int. Cl.$^4$ .................................................. A61B 5/02
[52] U.S. Cl. .................................... 128/675; 604/246; 604/256; 251/331
[58] Field of Search ............................ 128/672–673, 128/675, 748; 604/30, 32–34, 246–249, 256, 236–238; 251/331, 61.1; 137/510

[56] References Cited

U.S. PATENT DOCUMENTS

| | | | |
|---|---|---|---|
| 4,341,224 | 7/1982 | Stevens | 128/675 |
| 4,456,223 | 1/1984 | Ebling | 604/33 X |
| 4,501,300 | 2/1985 | Murphy | 604/246 X |
| 4,509,946 | 4/1985 | McFarlane | 128/673 X |
| 4,537,387 | 8/1985 | Danby et al. | 604/249 X |

Primary Examiner—Kyle L. Howell
Assistant Examiner—Angela D. Sykes
Attorney, Agent, or Firm—Donald N. Timbie

[57] ABSTRACT

A flush device in which a first passageway extends between a first opening in a body and a first port in said body, a second passageway extends between a second opening in said body and a second port in said body, a capillary pathway provides communication between said first and second passageways, a retainer for compressing a resilient pad into a sealing relationship with said ports and a projection is provided for pulling the pad away from the ports so as to open the seal between the pad and the ports and permit a large flow of fluid between said first and second passageways.

8 Claims, 5 Drawing Sheets

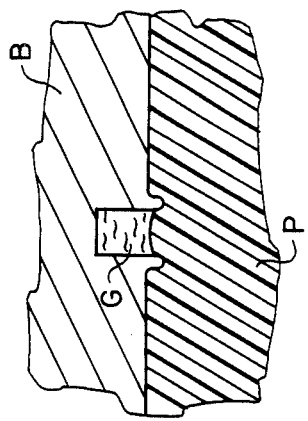
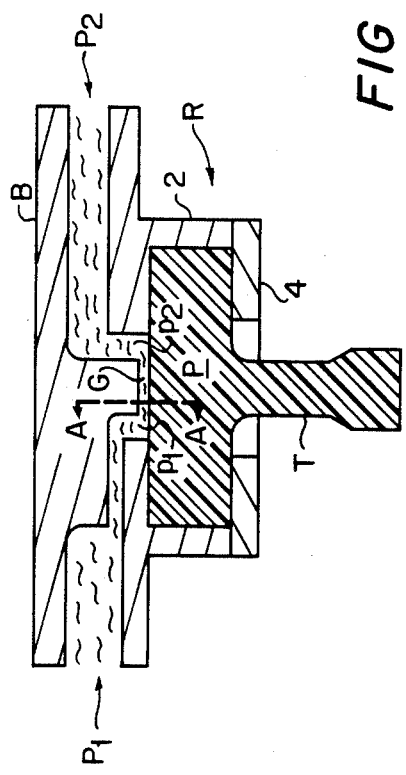
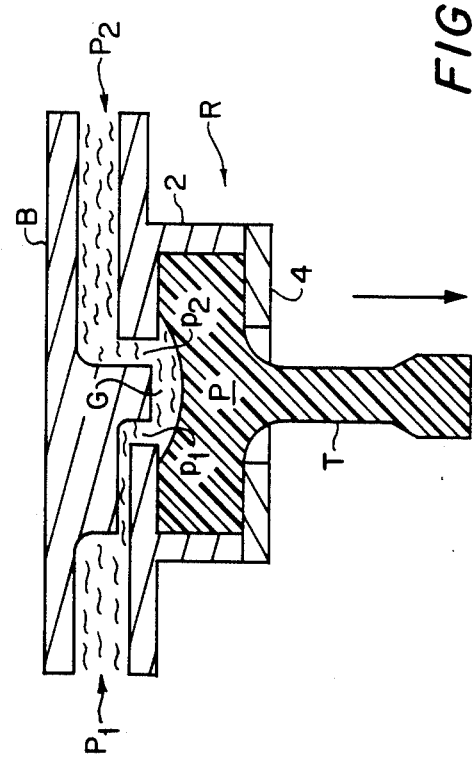

FLUSH DEVICE

BACKGROUND OF THE INVENTION

In monitoring the blood pressure of a patient at some point in a blood vessel, it is customary to connect one end of a catheter to a pressure dome, fill the dome and catheter with a saline solution, and insert the other end of the catheter through the blood vessel until it reaches the point of interest. In order to prevent the catheter from being clotted with blood, a slow flow of the saline solution is maintained through it. When, on occasion, blood samples are obtained by drawing blood through the catheter, the catheter is cleaned out by flushing it with a fast flow of the saline solution. In order to prevent injury to the patient, it is necessary that the fast flow be limited to brief intervals. Accordingly, devices have been designed that provide a continuous slow flow to prevent clogging and a fast flow to flush the catheter when activated by the clinician. The fast flow is automatically terminated by the device after deactivation so that fail-safe operation is attained.

When the dome and catheter are first filled with saline solution, the fast flow is used so as to reduce the time required in filling the system. In order to obtain good pressure measurements, it is essential that the dome and catheter be free from bubbles that might result from the filling process; but with prior art devices, it is difficult to eliminate them. Whereas capillary tubes have worked well as a means for providing the slow flow, the overall design of prior devices has been such as to form traps for bubbles.

BRIEF SUMMARY OF THE INVENTION

In accordance with this invention, a continuous slow flow is provided between first and second passageways in a plastic body by a capillary pathway, and a controlled fast flow is provided via ports in each passageway that are sealed by a resilient pad. The bottom surface of the pad may be flat or preferably slightly convex. It is compressed against the ports so that no flow normally occurs. A stem that is connected to the resilient pad provides means whereby it can be moved by an operator so as to open the seals between it and the ports and permit a large flow of fluid between the passageways. When the operator releases the stem, the resilient pad resumes its sealed position.

The capillary pathway can be provided by a groove in the outer surface of the plastic body that extends between the ports; but in a preferred embodiment, the capillary pathway is provided by a tube having a third passageway of small diameter extending through it. The tube is mounted within a fourth passageway that extends between the first and second passageways. This construction permits the tube to be positioned with its ends flush with the ends of the fourth passageway so as to prevent the formation of bubble traps.

A particularly advantageous feature of this preferred embodiment is the fact that a section of the fourth passageway is enlarged, and an aperture that communicates with this enlarged section is provided in the body of the device. After the tube is positioned in the fourth passageway, adhesive is injected into the aperture and around the tube so as to hold it in the adjusted position and block any flow along the outside of the tube.

BRIEF DESCRIPTION OF THE DRAWINGS

FIG. 5 is a cross-section of a flush device of this invention taken through the passageways and showing a groove as a means for permitting continuous slow flow and with the actuating means in such position as to prevent a large flow;

FIG. 5A is similar to FIG. 5 except that the actuating means is shown in a position permitting a large flow; and FIG. 5B is an enlarged section at AA of FIG. 5 in which the edges of the groove are raised.

DETAILED DESCRIPTION OF THE INVENTION

All corresponding parts are designated the same way in all of the drawings.

Figure 1A:
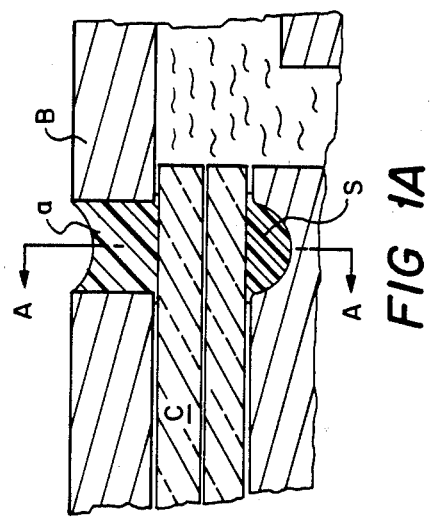
FIG. 1A is an enlarged view of the apertured area of FIG. 1.
Figure 1B:
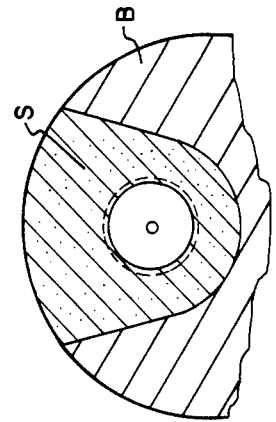
FIG. 1B is a cross-section at AA of FIG. 1A.
Figure 1:
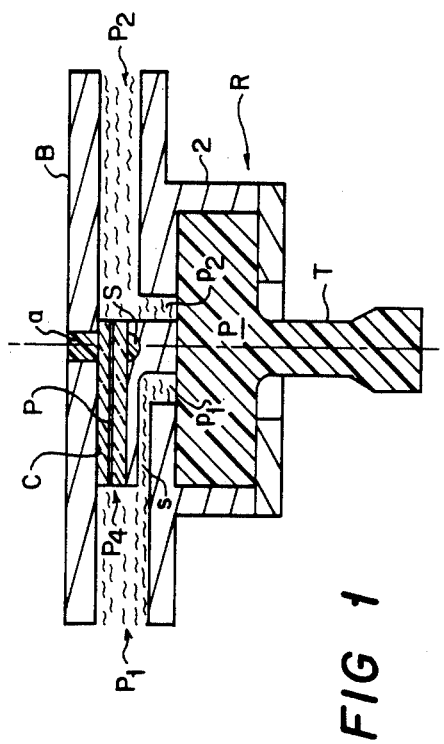
FIG. 1 shows a cross-section through all the passageways of a flushing device incorporating this invention when there is no large flow.

In FIG. 1, a molded plastic body B is shown as having two passageways P1 and P2 that are placed in communication by a capillary tube C, which is a tube having a passageway P3 extending therethrough of a sufficiently small diameter to restrict the flow of fluid to a desired slow rate. The tube C may be of circular or other cross-section and may be made of glass. A passageway P4 is provided into which the capillary tube C may be inserted with a small clearance so that its position can be adjusted. A section S of the passageway P4 is enlarged and communicates with an aperture a in the body B. The tube C is positioned so that its ends are flush with the ends of the passageway P4, thereby preventing the formation of pockets that trap bubbles. When the desired position is attained, an adhesive is injected into the aperture a so as to fill the enlarged space S. In addition to retaining the tube C in position, the adhesive prevents any fluid from passing between the capillary tube C and the passageway P4.

A retainer R, which may be comprised of a cylinder 2 and an annular cap 4, compresses a circular resilient pad P, that may be made of rubber, into a sealing relationship with ports p1 and p2 that respectively communicate with the passageways P1 and P2 so that the only flow through the device is via the passageways P1, P2 and P3. The ports p1 and p2 have a smaller cross-section than the passageways P1 and P2 and the port p1 includes the sections.

Figure 1C:
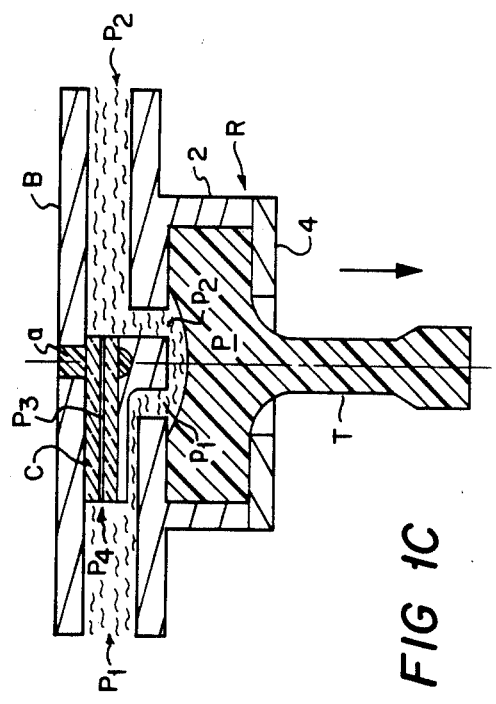
FIG. 1C illustrates the position of the resilient pad of FIG. 1 required to produce a large flow.

A tongue T is attached as by molding to the center of the pad P. A large flow is attained by pulling the tongue T as shown in FIG. 1C so as to pull the the resilient pad P away from the ports p1 and p2 and allow flow between those ports as well as through the passageways P1, P2, and P3.

It has been found that the flush device practically eliminates bubbles by itself when the flow is from P1 to P2. When the resilient pad P is in the relaxed position shown in FIG. 1, all air is excluded from the sealing interface between the pad P and the body B. When the pad P is activated, any bubbles are carried out of the device by the fluid flow.

Figure 2:
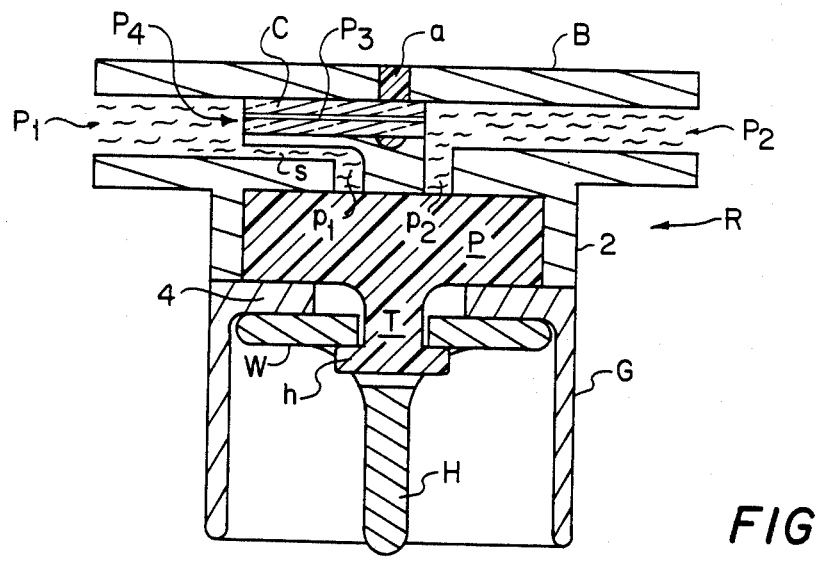
FIG. 2 is a cross-section that is the same as FIG. 1 but which additionally shows actuation means for obtaining a large flow when desired.
Figure 2A:
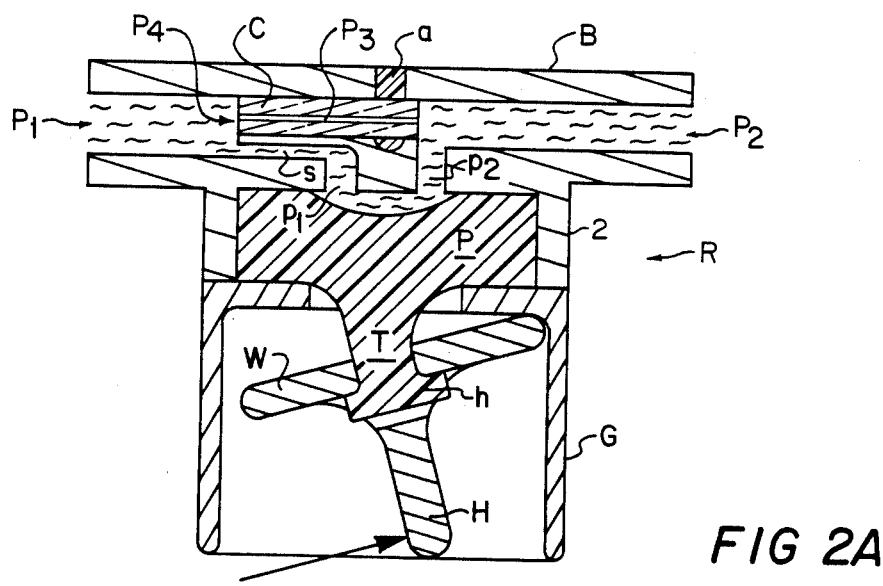
FIG. 2A is a cross-section like that of FIG. 2 in which the actuation means is positioned to produce a large flow.

FIGS. 2 and 2A include the structure of FIG. 1 but additionally illustrate actuating means for pulling the tongue T so as to permit a large flow. The tongue T extends through a stiff wafer W and is provided with a head h on the other side so as to prevent it from being pulled through the wafer. A toggle handle H is part of the wafer W. A cylindrical guard G is formed on the annular cap 4 so as to prevent the toggle handle H from being accidentally moved and to provide a fulcrum for the wafer W.

A large flow is obtained by pulling the toggle handle H to one side as illustrated in FIG. 2A. When the outer edge of the wafer W strikes the guard G, it starts to pivot so that further movement of the toggle handle H exerts a pull on the tongue T. As in FIG. 1, this opens the seal between the resilient pad P and the ports p1 and p2.

Figure 3:
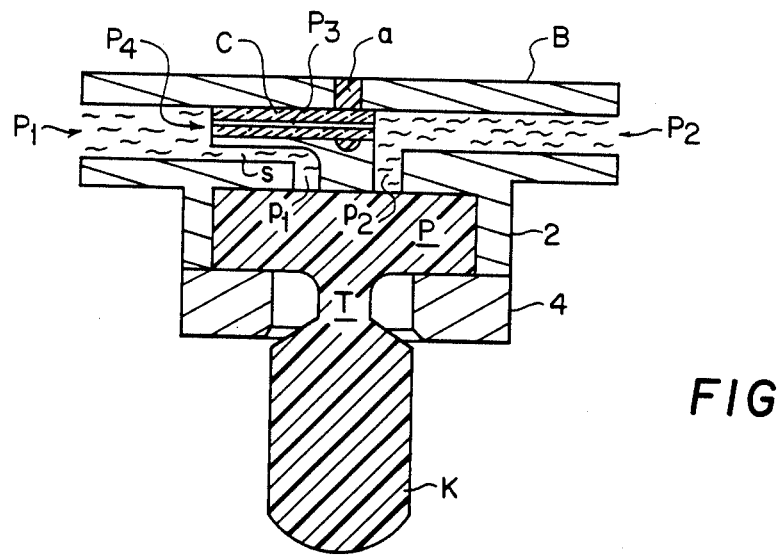
FIG. 3 is a cross-section of a flushing device of the invention taken through the passageways that illustrates a different kind of actuation means positioned so that no large flow occurs.
Figure 3A:
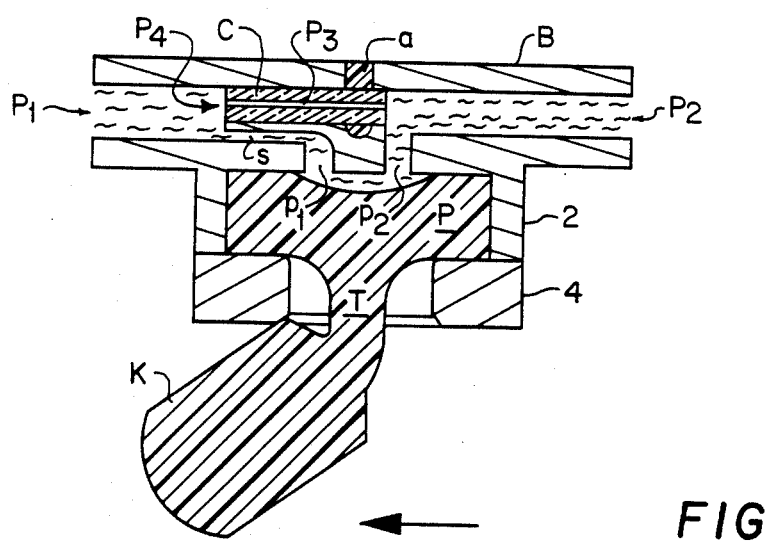
FIG. 3A is the same as FIG. 3 except that the actuation means is shown in a position causing a large flow.

FIGS. 3 and 3A illustrate another means for actuating the tongue T. The end of the tongue T is connected to a knob K of such dimension that when pushed to one side as illustrated in FIG. 3A, it will bear against the cap 4 and exert a pull on the tongue T so as to permit a larger flow.

Figure 4:
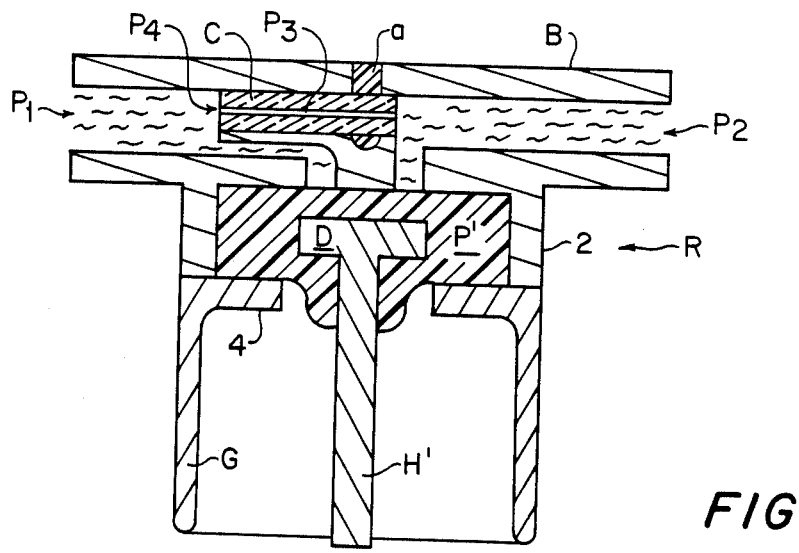
FIG. 4 is a cross-section taken through the passageways of a flush device having a different type of large flush actuator that is shown in a position where the large flow is prevented.
Figure 4A:
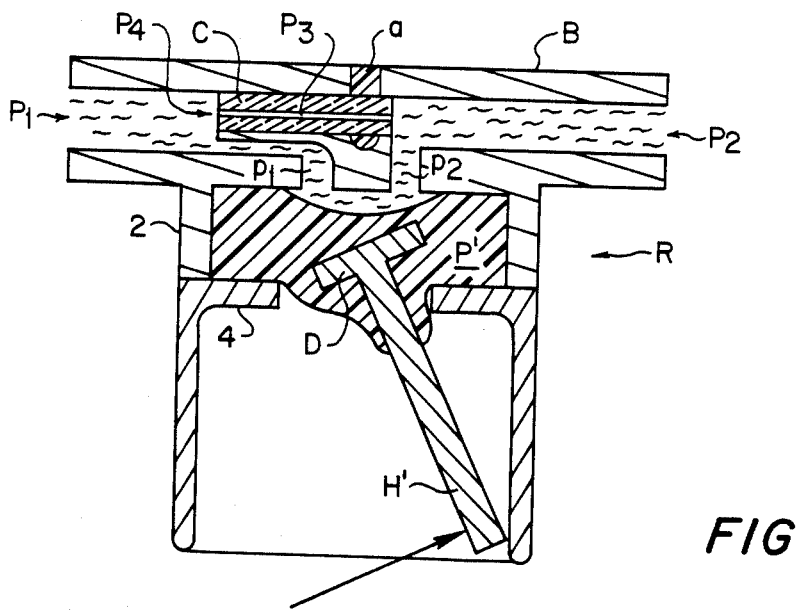
FIG. 4A is similar to FIG. 4 except that the actuator is shown in a position permitting large flow.

FIGS. 4 and 4A illustrate still another means for opening the seal between the ports p1 and p2. In this embodiment, a resilient pad p' is compressed by the cap 4 so as to force the pad P to seal the ports p1 and p2, and a toggle handle H' that is made of rigid material is provided with an enlarged disk D that is embedded in the pad P. When the toggle handle H' is pushed to one side as shown in FIG. 4A, it warps the pad P' so as to open the seal between it and the ports p1 and p2.

FIGS. 5 and 5A illustrate a flush device in which the slow flow is through a groove G formed in the exterior surface of the body B and extending between the ports p1 and p2. The resilient pad P is stiff enough to prevent its being forced into the groove G to any substantial degree by the compression exerted by the cap 4, and the ports p1 and p2 are sealed by the pad P so that no flow is permitted between them except that which passes through the groove G. The cross-section of the latter is small enough to provide a desired low flow. When the tongue T is activated, as in FIG. 5A, the seal between the pad P and the ports p1 and p2 is opened so as to permit a larger flow.

FIG. 5B shows a cross-section of the groove G at AA in FIG. 5, in which the edges of the groove G are raised so as to enhance the seal, but in some designs the raised edges can be omitted.

It will be understood that the passageway that provides communication between P1 and P2 and could be formed in the body B in any suitable manner e.g. by molding.

What is claimed:

1. A flush device comprising
   a body, having an outer surface
   means defining first and second openings in said body,
   means defining first and second ports in said body,
   means defining a first passageway between said first opening and said first port,
   means defining a second passageway having inner and outer ends, said second passageway extending between said second opening and said second port, said second port being at the inner end of said second passageway,
   means for defining a third passageway communicating between said first and second passageways,
   a resilient pad,
   means for compressing said pad against said outer surface so as to form a seal therewith between said ports, and
   means by which said pad can be pulled away from said ports so as to open the seal between said pad and said outer surface.

2. A flush device as set forth in claim 1 wherein said means defining said third passageway is a tube within said body, said tube having a capillary passageway contained therein.

3. A flush device as set forth in claim 2 having means defining a fourth passageway in said body communicating between said first and second passageways, and wherein
   said tube is mounted within said fourth passageway.

4. A flush device as set forth in claim 3 having means defining an enlarged section in said fourth passageway, and
   means defining an aperture in said body that communicates with said enlarged section whereby adhesive means can be forced into said enlarged section for holding said capillary tube in place and for providing a seal between said capillary tube and said fourth passageway.

5. A flush device as set forth in claim 3 wherein the end of said tube adjoining one of said first and second passageways is flush with the end of said, one passageway.

6. A flush device as set forth in claim 1 wherein said means defining said third passageway includes means defining a groove in the outer surface of said body that extends between said first and second ports said groove having edges.

7. A flush device as set forth in claim 6 wherein the edges of the groove are raised.

8. A flush device as set forth in claim 1 wherein said means defining said third passageway is contained within said body and wherein said latter means has a surface at the inner end of said second passageway that is free from pockets.

* * * * *